United States Patent
Young et al.

(10) Patent No.: US 8,459,265 B2
(45) Date of Patent: Jun. 11, 2013

(54) UNITARY STRUCTURED MULTI-TIER DRAPE

(75) Inventors: Christopher B. Young, Chattanooga, TN (US); Scott D. Hodges, Oultewah, TN (US); S. Craig Humphreys, Chattanooga, TN (US)

(73) Assignee: Variamed, LLC, Chattanooga, TN (US)

( * ) Notice: Subject to any disclaimer, the term of this patent is extended or adjusted under 35 U.S.C. 154(b) by 582 days.

(21) Appl. No.: 12/790,563

(22) Filed: May 28, 2010

(65) Prior Publication Data

US 2011/0247634 A1 Oct. 13, 2011

Related U.S. Application Data

(60) Provisional application No. 61/323,187, filed on Apr. 12, 2010.

(51) Int. Cl.
*A61B 19/08* (2006.01)
*A61B 19/12* (2006.01)

(52) U.S. Cl.
USPC ........... 128/849; 128/850; 128/851; 128/852; 128/853; 128/854; 128/855; 128/856

(58) Field of Classification Search
USPC .................................. 128/849–856
See application file for complete search history.

(56) References Cited

U.S. PATENT DOCUMENTS

| | | |
|---|---|---|
| 270,443 A | 1/1883 | Kraemer |
| 1,559,458 A | 10/1925 | Rizianu |
| 2,335,379 A | 11/1943 | Bersin et al. |
| D240,882 S | 8/1976 | Knight |
| 3,998,221 A | 12/1976 | Collins |
| 4,384,573 A | 5/1983 | Elliott |
| 4,476,860 A | 10/1984 | Collins et al. |
| 4,705,084 A | 11/1987 | Rodebaugh et al. |
| 4,938,522 A | 7/1990 | Herron et al. |
| 5,170,804 A | 12/1992 | Glassman |
| 5,460,440 A | 10/1995 | Moauro |
| 5,592,952 A | 1/1997 | Bohn |
| 5,871,015 A | 2/1999 | Lofgren et al. |
| 6,019,102 A | 2/2000 | Becker |
| 6,497,233 B1 | 12/2002 | DeAngelis |
| 2003/0233964 A1 | 12/2003 | Comeaux |
| 2004/0118410 A1 | 6/2004 | Griesbach, III |
| 2004/0194673 A1 | 10/2004 | Comeaux et al. |

FOREIGN PATENT DOCUMENTS

| | | |
|---|---|---|
| WO | 0141665 A1 | 6/2001 |
| WO | 2006127473 A2 | 11/2006 |
| WO | 2009049912 A1 | 4/2009 |

OTHER PUBLICATIONS

International Search Report, PCT/US2011/032088 (Apr. 12, 2011).
Written Opinion of the Interanational Searching Authority, PCT/US2011/032088 (Apr. 12, 2011).
"Sico Room Service and Mobile Catering Tables", SICO Incorporated, 7525 Cahill Road, PO Box 1169, Minneapolis, MN 55440 (1990).

*Primary Examiner* — Patricia Bianco
*Assistant Examiner* — Nihir Patel
(74) *Attorney, Agent, or Firm* — Baker Donelson

(57) ABSTRACT

A drape having a pair of elongated sheets connected at distal ends to define a skirt, with opposing side walls in a first portion of the elongated sheets having a first width and in a second portion having a different width so the drape has a stair-step structure, with a paper and plastic laminated first and second tier panels attached to the elongated sheets in spaced-relation and a central panel attached therebetween, for covering a tiered surgical operating table.

16 Claims, 2 Drawing Sheets

UNITARY STRUCTURED MULTI-TIER DRAPE

TECHNICAL FIELD

The present invention relates to surgical drapes. More particularly, the present invention relates to unitary drapes for covering tiered surgical operating tables.

BACKGROUND OF THE PRESENT INVENTION

Tiered surgical instrument tables provide medical personnel access to a surgical site of a patient as well as access to surgical equipment and supplies for use during a surgical procedure. For example, a tiered surgical table provides a lower tier supporting surface on which a patient may lie for surgery while an upper tier provides a supporting surface for placement of medical equipment and supplies.

It is important that the surgical theatre provide a sterile environment. In addition to conventional sterilization of surgical equipment and supplies, tables are often covered with surgical drapes to provide an insolating sterile surface on which to place surgical equipment and supplies as well as help isolate the surgical site. Surgical drapes are typically large sheets of a non-permeable material for controlling fluid flow but may provide absorbent materials for receiving and holding fluids during surgery.

Tiered surgical tables, while providing convenience of locating the patent in reasonable and accessible proximity to the medical equipment and supplies, present additional problems as to sterile operating surfaces. Often, several drapes sheets are placed in overlapping relation. One known surgical drape is provided for use with surgical tables having a lower tier and an upper tier at least partially extending over the lower tier surface. The drape isolates the sterile lower tier surface from a contaminated underside surface of the upper tier. The drape includes a bottom sheet that covers the lower tier and a top sheet that covers the upper tier. A middle sheet attaches to the top surface of the bottom sheet and to a front edge of the top sheet. The middle sheet spans the open gap between the two tiers in order to isolate the sterile lower tier surface from the underside surface of the top tier. However, this drape has drawbacks to its use, notably there are open gaps on the sides of the drape between the tiers and proper installation is not readily accomplished.

Accordingly, there is a need in the art for an improved drape to cover tiered surgical tables. It is to such that the present invention is directed.

BRIEF SUMMARY OF THE INVENTION

The present invention meets a need in the art for a structured surgical drape that covers a tiered surgical table by which vertically spaced surgical table surfaces are covered to define separate sterile operating surfaces. The structured surgical drape comprises a pair of elongated sheets connected at aligned distal ends to define a skirt for a drape, with a first one of the elongated sheets defining a first side wall and a back wall and a second one of the elongated sheets defining a second side wall opposing the first side wall and a front wall opposing the back wall. Each elongated sheet has a length exceeding a first width and each elongated sheet has a first portion of the first width and a second portion of a second width greater than the first width so that the first and second side walls thereby define a stepped structure. A pair of paper and non-permeable material laminated tier sheets attach to the elongated sheets. A first one of the tier sheets attaches on opposing sides to respective first edges of the first portion of the elongated sheets and a second one of the tier sheets attaches on opposing sides to respective edges of the second portion of the elongated sheets. A central panel attaches on opposing lateral sides to a respective transition edge of the elongated sheets between the first portion and the second portion thereof and attaches on opposing second sides to a respective inner edge of the first tier sheet and the second tier sheet, whereby the central panel is substantially normal to the first tier sheet so that the drape has a stair-step structure. The first and second side walls extend uninterrupted from the respective first edges to a free distal edge in a common plane remote from the first tier sheet.

Objects, advantages, and features of the present invention will become readily apparent upon reading the following detailed description in conjunction with the drawings and the appended claims.

DETAILED DESCRIPTION

Figure 1:
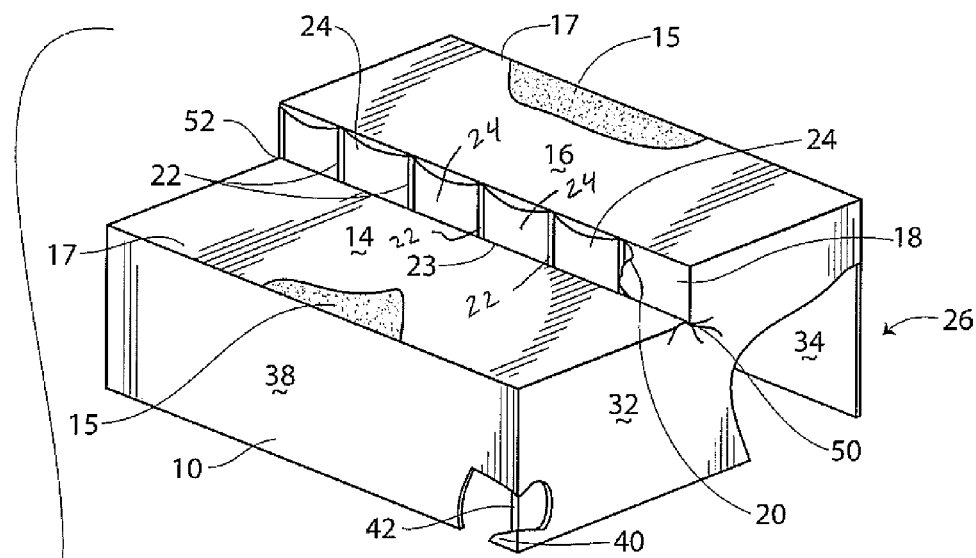
FIG. 1 illustrates a structured tiered surgical drape according to the present invention exploded from a tiered operating table.
Figure 1:
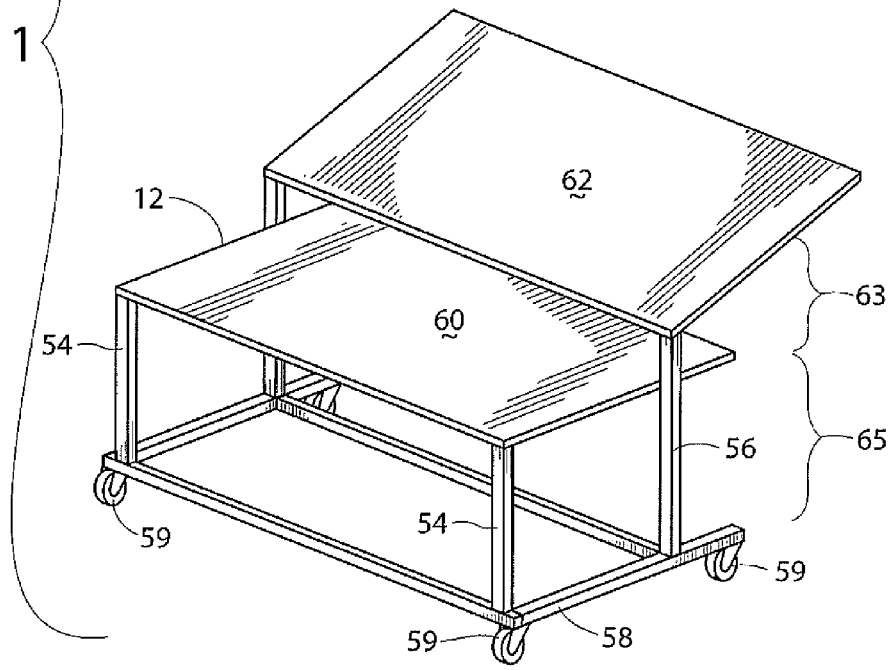

With reference to the drawings, in which like parts have like reference numerals, FIG. 1 illustrates in perspective view an exemplary embodiment of a structured tiered surgical drape 10 according to the present invention, exploded from a tiered surgical table 12. The surgical drape 10 comprises a fitted structured sheet having a first tier panel 14 and a second tier panel 16. As shown in cut-away view, the fitted structured drape 10 is open-bottom for being received by the surgical table 12 as discussed below. Each of the first tier panel 14 and the second tier panel 16 are made of a laminated sheet. The sheet has an absorbent layer 15 and a non-permeable material layer 17 as shown in cut-away view. In the illustrated embodiment, the laminated sheet is formed of a paper and a plastic sheet. Such laminated sheets are conventional with surgical drapes whereby the plastic sheet restricts fluid flow as a barrier between a surgical site on a patient and an upper surgical operating surface. The paper sheet absorbs fluids that may flow from the surgical site to resist leakage, drips and flows onto the surgical table, surgical equipment, and the surgical theatre.

A transparent central panel 18 attaches on opposing sides to a respective inward edge of the first tier panel 14 and of the second tier panel 16. In the illustrated embodiment, a second transparent central panel 20 overlies the central panel 18. The panels 18, 20 attach together at spaced-apart seams 22. The seams 22 define pockets generally 24 open at an edge proximate the second tier panel 16, with the opposing portions of the panels 18, 20 as side walls of the pockets. The pockets 24 receive articles during surgical procedures.

A skirt generally 26 extends about a perimeter of the drape 10. The skirt 26 in the illustrated embodiment assembles from a pair of opposing panels 28, 30, best illustrated in exploded perspective view in FIG. 2. The panel 28 defines a side wall 32 and back wall 34 of the drape 10. The panel 30 defines a side wall 36 opposing the side wall 32 and a front wall 38 opposing the back wall 34 of the drape 10. Each panel 28, 30 comprises an elongated sheet having a length exceeding a width. Each side wall 32, 36 has a first portion 29 of a first width and a second portion 31 of a second width greater from the first width so that side walls thereby define a stepped structure.

Figure 3:
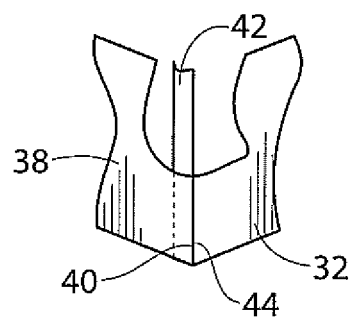
FIG. 3 illustrates in detailed perspective view an interior seamed connection between adjacent panels of the structured tiered surgical drape illustrated in FIG. 1.

The first tier panel 14 and the second tier panel 16, the central panels 18, 20 and the opposing panels 28, 30, attach together at respective adjacent edges with interior welded seams. By way of exemplary illustration, FIG. 3 shows in detailed perspective view an interior seamed connection generally 40 between the adjacent side edges of the front wall 38 and of the side wall 32. A side edge portion 42 of the front wall 38 extends as a flap inwardly. A side edge 44 of the side wall 32 aligns with a portion of the flap. A beating tool momentarily applied to the aligned overlapped portion 42 and side edge 44 secures the connection of the front wall 38 and the side wall 32. The flap 42 extends inwardly to define the interior seamed connection 40 between the adjacent panels 28, 30. The welds may be heat formed welds, sonic formed welds, or other suitable securing process so that the seam blocks fluid flow therethrough. Adhesive bonding is not as desirable due to potential seam separation. It is appreciated that both aligned sheets can extend as flaps inwardly of the seam.

With continuing reference to FIG. 1, each of the side panels 28, 30 defines a gathered portion generally 50, 52 at a corner edge where the first tier panel 14 and the central panel 18 connect with an interior welded seam. The gathered portions 50, 52 enables the central panel 18 to be disposed substantially normal or perpendicular to the first and second tier panels 28, 30, so that the fitted draped 10 can be placed over the tiered surgical table 12, as discussed below.

The surgical table 12 in the exemplary illustration has vertical posts 54, 56 (three posts are illustrated) on opposing sides, which posts extend from a foundation or base 58 formed of interconnected members. The foundation can have feet, or as illustrated, castors 59, for flexible mobility of the tiered surgical table 12. The posts 54, 56 support a vertically spaced lower tier surgical deck 60 and an upper tier surgical deck 62. The lower tier deck 60 connects to the posts 54, 56. The upper tier deck is supported by members (not illustrated) that connect to the posts 56. The decks 60, 62 define a gap 63 with a second gap 65 between the foundation 58 and the lower deck 60. Structure can be provided for adjusting the angle of orientation of the upper tier deck 62 or the gap 63 relative to the lower tier deck 60. The drape 10 in side view thereby defines a stair-step structure to accommodate the vertical spacing of the tiered surgical decks 60, 62 of the surgical table 12.

Figure 2:
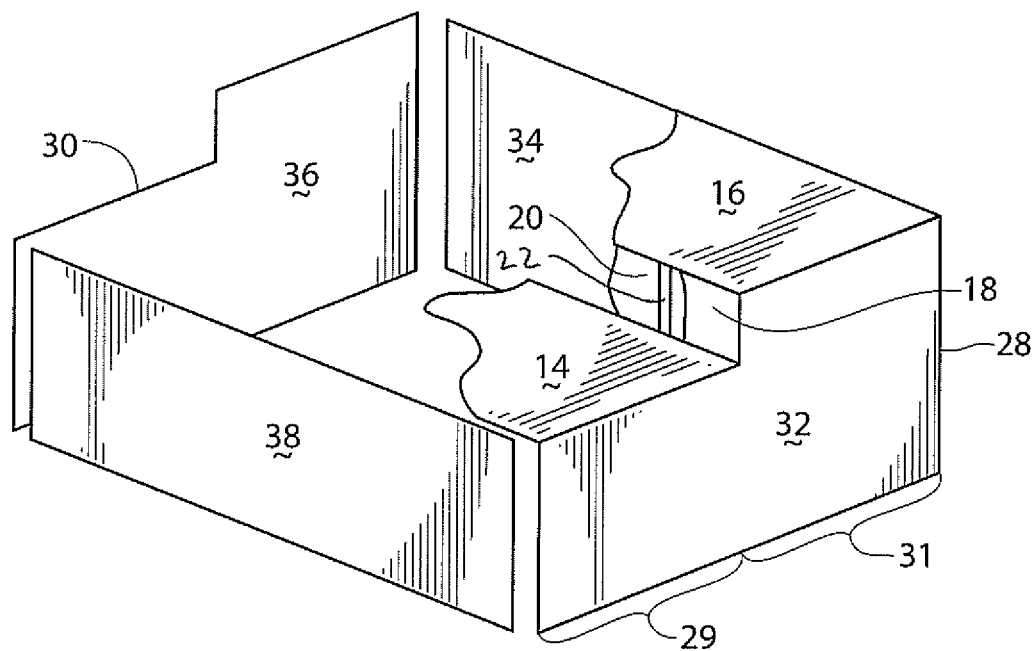
FIG. 2 illustrates in side perspective view a pair of opposing panels exploded apart which panels form opposing sides and opposing front and back portions of a skirt extending about a perimeter of the drape.

With reference to FIG. 2, the panels 28, 30 attach together at a front edge of the side wall 32 and a side edge of the front wall 38. Similarly the panels 28, 30 attach together at a side edge of the back wall 34 and a back edge of the side wall 36. Respective upper edges of the panels 28, 30 attach to side edges of the first tier panel 14 and the second tier panel 16 (shown in cut-away view). The opposing edges of the central panel 18 attach to adjacent inward edges of the first tier panel 14 and the second tier panel 16. Opposing lateral side edges of the central panel 18 attach to the step edge of the panels 28, 30. The outward edges of the first tier panel 14 and the second tier panel 16 attach to adjacent upper edges of the panels 28, 30.

With continuing reference to FIG. 1, the drape 10 provides a fitted structural covering for defining sterile operating surfaces 14, 16 supported by the surgical decks 60, 62 of the tiered surgical table 12. The drape 10 is provided conventionally in a sterile package such as in a folded compact size, for example, the opposing side walls 32, 36 and the opposing front and back walls 38, 34 fold against the inner surfaces of the first tier panel 14 and the second tier panel 16. The drape 10 can then be folded to a more compact size, for example, by accordion-folding the folded assembly of the walls and the tier panels.

For use, the drape 10 is removed from the sterile package and placed on the surgical table 12. The drape 10 is unfolded so that the paper surface of the first tier panel 14 and the second tier panel 16 are towards the surgical decks 60, 62. The gathers 50, 52 of the side panels 28, 30 structure the fitted drape 10 to define vertically-spaced lower and upper covers (using the first and second tier panels 14, 16) on the decks 60, 62 for the tiered surgical table 12 with the central panel 18 disposed substantially normal to at least one of the first tiered panel 14 or second tiered panel 16. The drape 10 is extended to dispose the lateral sides proximate the sides of the surgical table. The skirt 26 is disposed to cover the gaps 63 and 65 with a distal edge of the skirt intermediate the foundation 58 and the deck 60. The side walls 32, 36 and the back and front walls 34, 38 extend a substantial distance below the lower deck 60 of the surgical table 12.

The pockets 24 on the central panel 18 provide convenient and observable spaces for placing articles used during surgery. It is to be appreciated that the front wall 38 can also similarly include an overlying transparent sheet selectively attached to the front wall with seams to define a plurality of pockets. The transparent pockets permit a surgeon or nurse to inspect the contents, for example, for accounting for equipment used during surgery.

The structural fitted drape 10 includes side panels that extend between the first tier panel 14 and the second tier panel 16 and below, so that the gap 63 between the upper tier and the lower tier of the operating table 12 is closed and a portion of the gap 65 between the lower tier and the foundation 58 is covered. The side panels 28, 30 thus extend from the second tier panel 16 uninterrupted between the first tier panel 14 and the second tier panel 16, and further to a free distal edge that is beyond and remote from the first tier panel.

The drape 10 is used on tiered surgical operating tables 12 having a lower tier surface and a vertically spaced upper tier surface. The first tier panel 14 and the second tier panel 16 lie on respective tier surfaces of the lower and upper decks 60, 62 with the central panel 18 disposed in a substantially vertical plane to span a vertical gap between the tiers. The side walls cover the open lateral sides or gaps 63 of the surgical operating table as well as at least a portion of the gap 65 between the lower deck 60 and the foundation 58.

The drape 10 of the present invention is unitary, in that the drape provides the single fitted structure with tier panels attached in spaced-apart relation intermediate a central panel to skirt defining sheets joined together at adjacent edges to isolate the tiered surgical operating table having the lower surgical surface and the vertically spaced upper surgical surface.

The apparatus and methods disclosed herein can be made and executed without undue experimentation in light of the present disclosure. While the apparatus of this invention have been described in terms of illustrated embodiments, it will be apparent to those of skill in the art that variations may be applied to the apparatus and in the process described herein without departing from the concept, spirit and scope of the invention. All such similar substitutes and modifications apparent to those skilled in the art are deemed to be within the spirit, scope and concept of the invention as defined by the appended claims.

What is claimed is:

1. A drape for a tiered surgical operating table, comprising:
a pair of elongated sheets connected at aligned distal ends to define a skirt for a drape, a first one of the elongated sheets defining a first side wall and a back wall and a second one of the elongated sheets defining a second side wall opposing the first side wall and a front wall opposing the back wall, each elongated sheet having a length exceeding a width and each elongated sheet having a first portion of a first width and a second portion of a second width greater from the first width so that side walls thereby define a stepped structure;
a pair of paper and non-permeable material laminated tier sheets, a first one of the tier sheets attached on opposing sides to respective first edges of the first portion of the elongated sheets and a second one of the tier sheets attached on opposing sides to respective edges of the second portion of the elongated sheets;
a central panel attached on opposing lateral sides to a respective transition edge of the elongated sheets between the first portion and the second portion thereof and attached on opposing second sides to a respective inner edge of the first tier sheet and the second tier sheet, whereby the central panel is substantially normal to the first tier sheet so that the drape has a stair-step structure; and
the first and second side walls extending uninterrupted from the respective first edges to a free distal edge in a common plane remote from the first tier sheet.

2. The drape as recited in claim 1, wherein adjacent edges of the elongated sheets, the tier sheets and the central panel are joined by an inwardly formed weld connection.

3. The drape as recited in claim 2 wherein the weld connection is a heat weld.

4. The drape as recited in claim 2, wherein the weld connection is a sonic weld.

5. The drape as recited in claim 1, further comprising a second central panel attached to the first central panel at a plurality of spaced-apart seams to define a plurality of packets for receiving articles during surgery.

6. The drape as recited in claim 5, wherein the second central panel is transparent.

7. The drape as recited in claim 1, wherein the elongated sheets define gathers of sheet proximate the transition edge connection with the first tier sheet to facilitate disposing the central panel substantially normal to the first tier sheet.

8. The drape as recited in claim 1, wherein the non-permeable material is a plastic sheet.

9. A drape for a tiered surgical operating table, comprising:
a skirt having at least two elongated non-permeable sheets connected at aligned distal ends to define a pair of opposing side walls, a front wall, and a back wall, each of the opposing side walls having a first portion of a first width and a second portion of a second width greater from the first width so that side walls thereby define a stepped structure;
a first tier sheet and a second tier sheet, each formed of a paper sheet and a non-permeable material sheet laminated together, the first tier sheet attached on opposing side edges to respective edges of the first portion of the side walls, and the second tier sheet attached on opposing side edges to respective edges of the second portion of the side walls;
a central panel attached on opposing lateral sides to a respective transition edge of the side walls between the first portion and the second portion thereof and attached on opposing second sides to a respective inner edge of the first tier sheet and the second tier sheet, whereby the central panel is substantially normal to the first tier sheet so that the drape has a stair-step structure; and
the first and second side walls extending uninterrupted from the respective first edges to a free distal edge in a common plane remote from the first tier sheet.

10. The drape as recited in claim 9, wherein adjacent edges of the elongated sheets, the tier sheets and the central panel are joined by an inwardly formed weld connection.

11. The drape as recited in claim 10 wherein the weld connection is a heat weld.

12. The drape as recited in claim 10, wherein the weld connection is a sonic weld.

13. The drape as recited in claim 9, further comprising a second central panel attached to the first central panel at a plurality of spaced-apart seams to define a plurality of packets for receiving articles during surgery.

14. The drape as recited in claim 13, wherein the second central panel is transparent.

15. The drape as recited in claim 9, wherein the elongated sheets define gathers of sheet proximate the transition edge connection with the first tier sheet to facilitate disposing the central panel substantially normal to the first tier sheet.

16. The drape as recited in claim 9, wherein the non-permeable material is a plastic sheet.

* * * * *